United States Patent [19]

Rebafka et al.

[11] 4,386,208

[45] May 31, 1983

[54] PREPARATION OF N-ALKYLPIPERIDINES AND N-ALKYLPYRROLIDINES

[75] Inventors: Walter Rebafka, Eppelheim; Jüergen Schossig, Mannheim; Wolfgang Reiss, Ludwigshafen; Dieter Voges, Mannheim, all of Fed. Rep. of Germany

[73] Assignee: BASF Aktiengesellschaft, Fed. Rep. of Germany

[21] Appl. No.: 283,651

[22] Filed: Jul. 15, 1981

[30] Foreign Application Priority Data

Jul. 26, 1980 [DE] Fed. Rep. of Germany ....... 3028384

[51] Int. Cl.³ ............................................. C07D 295/02
[52] U.S. Cl. ...................................... 546/184; 548/579
[58] Field of Search ...................... 546/184; 260/326.8; 548/579

[56] References Cited

U.S. PATENT DOCUMENTS 2,837,524 6/1958 Oberrauch .......................... 546/184

FOREIGN PATENT DOCUMENTS 763666 12/1956 United Kingdom ................. 546/184

OTHER PUBLICATIONS

Paden, J. et al., *J.A.C.S.*, 58, (1936), 2487.

*Primary Examiner*—Richard A. Schwartz
*Attorney, Agent, or Firm*—Keil & Witherspoon

[57] ABSTRACT

N-Alkylpiperidines or N-alkylpyrrolidines are obtained by hydrogenating a corresponding N-alkyldicarboxylic acid imide over a fixed catalyst by first working to only partial conversion, for example of about 50%, and distilling off the required product together with water from the partially converted mixture, where appropriate with recycling of the unconverted remainder.

7 Claims, No Drawings

PREPARATION OF N-ALKYLPIPERIDINES AND N-ALKYLPYRROLIDINES

Whilst the hydrogenation of N-unsubstituted cyclic imides of monocarboxylic acids and dicarboxylic acids is well known and in some cases practised on an industrial scale (cf., for example, French Pat. No. 1,475,961; a similar case is described in German Laid-Open Application DOS No. 2,514,004, which concerns hydrogenation of a dicarboxylic acid dinitrile), the preparation of N-substituted pyrrolidines and piperidines has hitherto only been achieved either by hydrogenating and N-alkylation of unsubstituted succinimides and glutarimides, respectively, in alcohols (which thus act as solvents and alkylating agents), or by hydrogenating the dicarboxylic acid N-alkyl-imides with special catalysts, in dioxane as the solvent (cf. USSR Patent No. 259,889, and Paden and Adkins, J. Amer. Chem. Soc., 58 (1936), 2487).

A special case, which cannot be generalized, is the hydrogenation of butyrolactam (pyrrolidone) over a sintered cobalt metal catalyst; this leads to N-butylpyrrolidine (cf. German Laid-Open Application DOS No. 1,670,056), and is thus accompanied by a complicated rearrangement reaction of unknown course.

There is accordingly a need for a process for the preparation of N-alkylpyrrolidines and N-alkylpiperidines by hydrogenating the corresponding dicarboxylic acid imides, which can be carried out without extraneous solvents or similar auxiliaries (except for the catalyst).

In a close investigation of the course of the reaction, we have now found that on incomplete conversion, in the presence of a suitable catalyst, intermediates having a very high boiling point are formed, but that these can, after an appropriate separation operation, be recycled and converted completely. When these intermediates are separated off, water, inter alia, is removed with the desired products.

Accordingly, the essence of the invention is that to achieve a high rate of conversion and high yield, the reaction is taken to incomplete conversion, for example the reaction mixture is cycled, at appropriate velocity, over a fixed catalyst and means are provided, in the cycle system, by means of which completely converted constituents and incompletely converted or unconverted constituents, of the mixture can be separated from one another and from the water they contain. Thin film evaporators are examples of suitable means of this type.

The conversion per pass, in continuous operation, can be from 10 to 90% and is advantageously about 50% or less.

The achievement of this object is assisted by the use of suitable catalysts, cobalt catalysts being particularly advantageous. These catalysts, in contrast to the copper chromite catalysts described by Adkins, appear to be active even in the presence of water, and thus permit dispensing with the use of dehydrating solvents (cf. Adkins, J. Amer. Chem. Soc., loc. cit.). Some copper catalysts and nickel catalysts, of various compositions and make-ups, suitable for carrying out the process are also known.

It is preferred to use unsupported catalysts which in particular contain cobalt, and preferably contain small amounts of, for example, copper, manganese and phosphoric acid. However, the process can also be carried out with catalysts which contain cobalt, with or without other constituents, on a carrier; the latter can be, for example, aluminum oxide.

The catalysts are employed in catalytically active amounts, which depend, in a known manner, on the particular technology employed.

The reaction proceeds at a satisfactory rate at about 150°–250° C. and under a pressure of, for example, from 50 to 500 bar. In general, the yield exceeds 70% of the theoretical yield.

N-Alkylpyrrolidines and N-alkylpiperidines, where alkyl is, for example, of 1 to 20 carbon atoms, are used as intermediates for crop protection agents, as catalysts for the preparation of polyurethane plastics, and also, for example, as special bases in drugs. The compounds can also carry additional substituents on the carbon atoms of the ring structure, for example alkyl or alkoxymethyl groups.

The procedures described in the Examples given below in some cases do not represent the complete process but instead, for example, operate without recycling in certain instances, so that the composition of the reaction mixture on a simple, ie. single, pass can be determined. Examples 6 and 7 show complete operating cycles.

EXAMPLES 1 TO 3

The experiments were carried out in a conventional high pressure experimental tubular reactor, in each case charged with an unsupported catalyst, in 6 mm diameter extrudate form, consisting of 64% of cobalt oxide, 18% of copper(II) oxide, 7% of manganese(II,III) oxide and 4% of phosphoric acid, under a hydrogen pressure of 250 bar.

Various methods of operation (upward or downward), quantities etc. were employed. The conditions and results are shown in the Table.

TABLE

| Experiment No. (operating direction) | Reactor size (l) | Nature+ and amount of starting material | | Temp. (°C.) | Conversion per pass (%) | Yield (total conversion) (%) |
|---|---|---|---|---|---|---|
| 1 (↓) | 8 | 1.5 l/h | 33% of NMS | 230 | | 75 (100) |
| | | | 67% of NMG | | | 70 (80) |
| 2 (↑) | 2.2 | like 1 | | 240 | | 72 (100) |
| | | | | | | 75 (100) |
| 3 (↓) | 2.2 | 0.1 l/h | 20% of NES | 200 | | 60 (100) |
| | | | 30% of NEG | | | 80 (100) |

TABLE-continued

| Experiment No. (operating direction) | Reactor size (l) | Nature+ and amount of starting material | Temp. (°C.) | Conversion per pass (%) | Yield (total conversion) (%) |
| --- | --- | --- | --- | --- | --- |
| | | 50% of NEPP++ | | | |

+NMS = N—methylsuccinimide;
 NMG = N—methylglutarimide;
 NEG = N—ethylglutarimide;
 NES = N—ethylsuccinimide;
 NEPP = N—ethylpiperidine
++as solvent

EXAMPLE 4

2.2 liters of a cobalt catalyst containing 17% of cobalt oxide on an aluminum oxide carrier, in the form of 4 mm thick extrudates, were introduced into the apparatus used for Examples 2 and 3.

After conventional pretreatment with hydrogen, the catalyst was charged, at 210° C., with 100 ml per hour of a mixture of N-methylsuccinimide (NMS) and N-methylglutarimide (NMG), in the weight ratio of 35:65, which contained about 6% of water. The hydrogen pressure was kept at 250 bar.

Under these conditions, a conversion of about 76% was observed in each case; the yield, based on converted starting materials, reached 70%.

EXAMPLE 5

The procedure described above was followed, using a catalyst consisting of 6 mm thick extrudates of pure cobalt oxide.

The mixture introduced (NMS and NMG in the ratio 4:6) contained 7% of water.

At a conversion of 50%, a selectivity of 68% (NMS) and 70% (NMG) was achieved.

EXAMPLE 6

A vertical tubular high pressure reactor for continuous operation was filled with 10 liters of the catalyst described in Examples 1 to 3, and the conditions were set to a reaction temperature of 210° C. and a hydrogen pressure of 250 bar. 3 liters per hour of the crude mixture used in Example 5 (NMS and NMG in the ratio 4:6) were introduced from above and sufficient of the issuing liquid was admixed to the feed to give a throughput per unit area of 30 (m$^3$/m$^2$.h, based on the empty reactor). The recycled liquid was cooled to enable the reaction temperature to be maintained.

The remaining amount of liquid which issued was heated to 180° C. in a falling film evaporator, operated under atmospheric pressure, thereby removing water and low-boiling products. The amount of these was about 28% of the issuing liquid.

The high-boiling constituents proved to be virtually non-distillable (a temperature above 200° C. was required under 0.1 mbar); they were mixed with fresh NMS/NMG mixture and recycled to the reactor. Under steady state conditions, the amount of these high-boiling products proved constant, so that it follows that they are to be regarded as intermediates which, on further conversion, also give the desired products.

The distillate obtained from the falling film evaporator contained 4 parts by weight of N-methylpyrrolidine and 6.4 parts by weight of N-methylpiperidine in addition to 17 parts by weight of water and by-products.

Extrapolated to complete conversion, this amounts to a selectivity (yield) of about 85% in each case.

EXAMPLE 7

A vertical tubular high pressure reactor for continuous operation is filled with 3 liters of the catalyst described in Examples 1 to 3 and operated at follows, at 210° C. and under a hydrogen pressure of 250 bar: 1.2 liters/hour of a mixture consisting of 0.4 liter of N-methylsuccinimide and 0.8 liter of the distillation residue from the distillative working-up described below are introduced into the reactor from above. In order to remove the heat of reaction generated, sufficient of the issuing liquid is recycled to the top of the reactor to give a throughput per unit area of 30 m$^3$/m$^2$.h (based on empty reactor cross-section).

The remainder of the issuing liquid is heated to 170° C. in a falling film evaporator operating under atmospheric pressure, essentially causing the water formed, and the desired product N-methylpyrrolidine, to distil off. In continuous operation under these conditions, 0.5 liter/hour of distillate and 0.8 liter/hour of a high-boiling distillation residue are obtained. The latter is mixed with fresh N-methylsuccinimide in the ratio stated above and recycled to the reactor.

Under steady state conditions, the amount of these high-boiling products proves constant, so that it follows that they are to be regarded as intermediates which, on further conversion, also give the desired products. It is noteworthy that this distillation residue contains less than 5% of the starting material, and there is also no starting material in the distillate.

Analysis of the distillate obtained shows a yield of 78% of N-methylpyrrolidine, based on the 0.4 liter/hour of N-methylsuccinimide introduced.

We claim:

1. A process for the preparation of an N-alkylpiperidine or N-alkylpyrrolidine from a dicarboxylic acid N-alkylimide by hydrogenation, the acid having a carbon chain length of 4 or 5 and the alkyl substituent being of 1 to 20 carbon atoms, which comprises:
   (a) hydrogenating the dicarboxylic acid N-alkylimide in a reactor having a fixed bed hydrogenation catalyst;
   (b) removing the reactant from the reactor prior to complete conversion;
   (c) separating the product of (b) by distillation into a distillate containing the N-alkylpiperidine or N-alkylpyrrolidine product and water, and a high boiling residue containing both partially hydrogenated and unconverted dicarboxylic acid N-alkylimide; and (d) recycling said residue into the hydrogenation reactor; wherein the space velocity of the reactants through the reactor is controlled to limit conversion to 10–90% of theory, whereby the higher concentration of reactant and the removal of water of reaction result in a high over-all rate of conversion and a high yield.

2. A process as claimed in claim 1, wherein the catalyst consists of, or contains, cobalt.

3. A process as claimed in claim 1, wherein the alkyl group is of 1 to 5 carbon atoms.

4. A process as claimed in claim 1, wherein the catalyst contains cobalt, copper, manganese and phosphorus.

5. The process recited in claim 1 wherein the dicarboxylic acid N-alkylimide is hydrogenated in the liquid state.

6. The process recited in claim 1 wherein conversion per pass is less than or equal to 50%.

7. The process recited in claim 1 wherein hydrogenation takes place at a temperature of about 150°–250° C. and under a pressure of from 50 to 500 bar.

* * * * *